US010747399B1

United States Patent
Young et al.

(10) Patent No.: US 10,747,399 B1
(45) Date of Patent: Aug. 18, 2020

(54) APPLICATION THAT ACTS AS A PLATFORM FOR SUPPLEMENT APPLICATIONS

(71) Applicant: Allscripts Software, LLC, Raleigh, NC (US)

(72) Inventors: Ohad Young, Hod Hasharon (IL); Mary Sumner Johnson, Raleigh, NC (US); Ross Carlyle Teague, Cary, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 571 days.

(21) Appl. No.: 15/361,823

(22) Filed: Nov. 28, 2016

Related U.S. Application Data

(60) Provisional application No. 62/300,712, filed on Feb. 26, 2016.

(51) Int. Cl.
  *G06F 3/0482* (2013.01)
  *G16H 40/63* (2018.01)
  *G16H 10/60* (2018.01)

(52) U.S. Cl.
  CPC ......... *G06F 3/0482* (2013.01); *G16H 10/60* (2018.01); *G16H 40/63* (2018.01)

(58) Field of Classification Search
  CPC ....... G16H 10/60; G16H 40/63; G06F 3/0482
  See application file for complete search history.

(56) References Cited

U.S. PATENT DOCUMENTS

| 8,949,427 B2 | 2/2015 | Dubbels et al. |
| 2007/0174079 A1* | 7/2007 | Kraus ............... G06Q 10/10 705/3 |
| 2009/0177495 A1 | 7/2009 | Abousy et al. |
| 2011/0288877 A1 | 11/2011 | Ofek et al. |
| 2012/0215560 A1 | 8/2012 | Ofek et al. |
| 2012/0221535 A1 | 8/2012 | Dubbels et al. |
| 2013/0218596 A1 | 8/2013 | Gome et al. |
| 2014/0215490 A1* | 7/2014 | Mathur ............ G06F 19/328 719/313 |
| 2014/0350954 A1 | 11/2014 | Ellis et al. |
| 2015/0025911 A1 | 1/2015 | Altebrando et al. |
| 2016/0132645 A1* | 5/2016 | Charpentier ......... G16H 10/60 705/3 |

* cited by examiner

*Primary Examiner* — Ajay M Bhatia
*Assistant Examiner* — Mong-Shune Chung
(74) *Attorney, Agent, or Firm* — Medley, Behrens & Lewis LLC

(57) ABSTRACT

Described herein are various technologies pertaining to a graphical user interface (GUI) for a hub application that is displayed concurrently on a display with a graphical user interface (GUI) for a client electronic health record application (EHR). The hub application includes a ribbon that comprises several selectable buttons that respectively represent supplement applications, wherein a supplement application is configured to generate events based upon a current context of the client EHR. The GUI of the hub application is updated when a supplement application reports an update to the hub application, wherein the update to the GUI can include rendering a badge on a button that represents the supplement application.

20 Claims, 12 Drawing Sheets

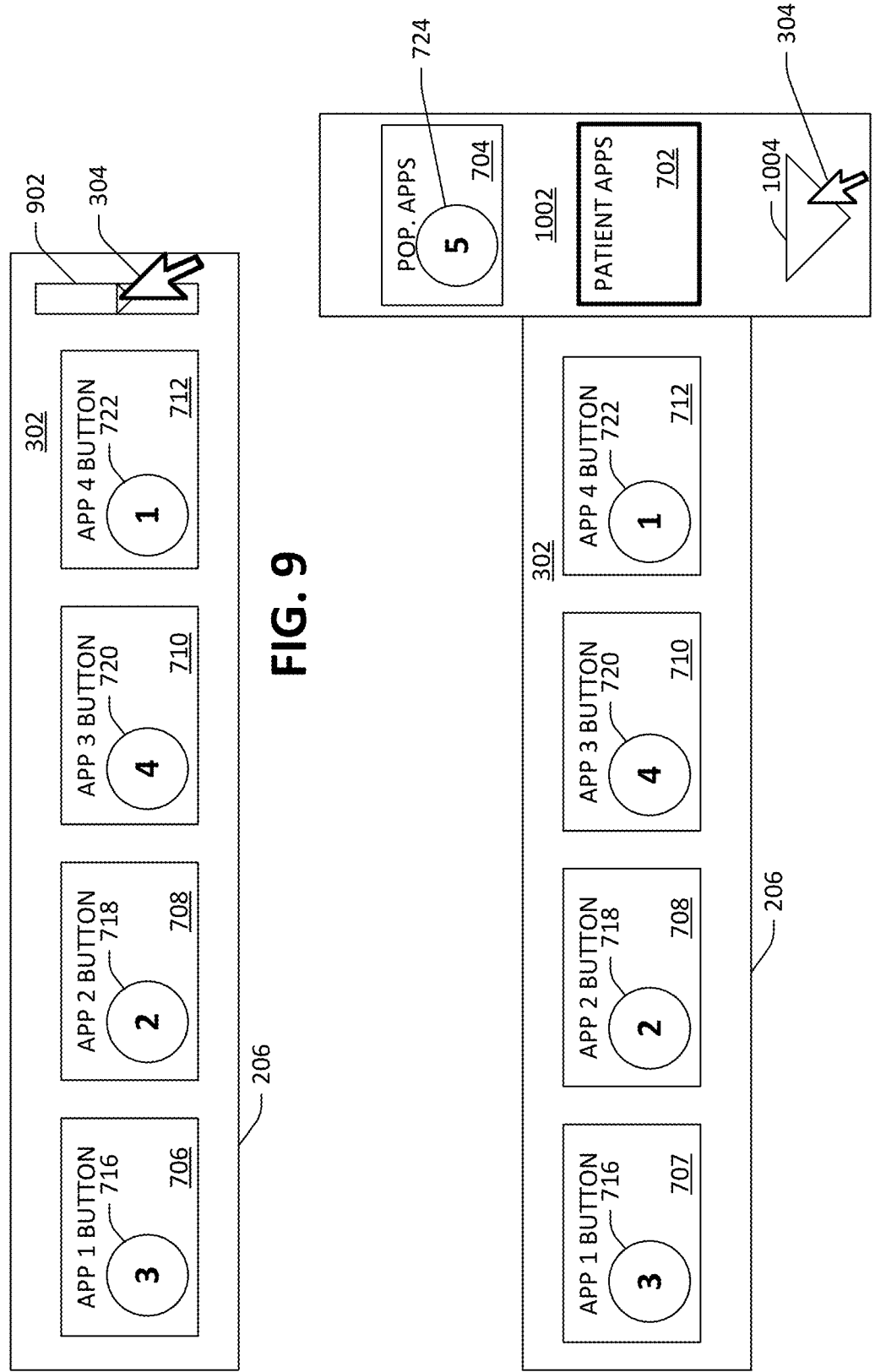

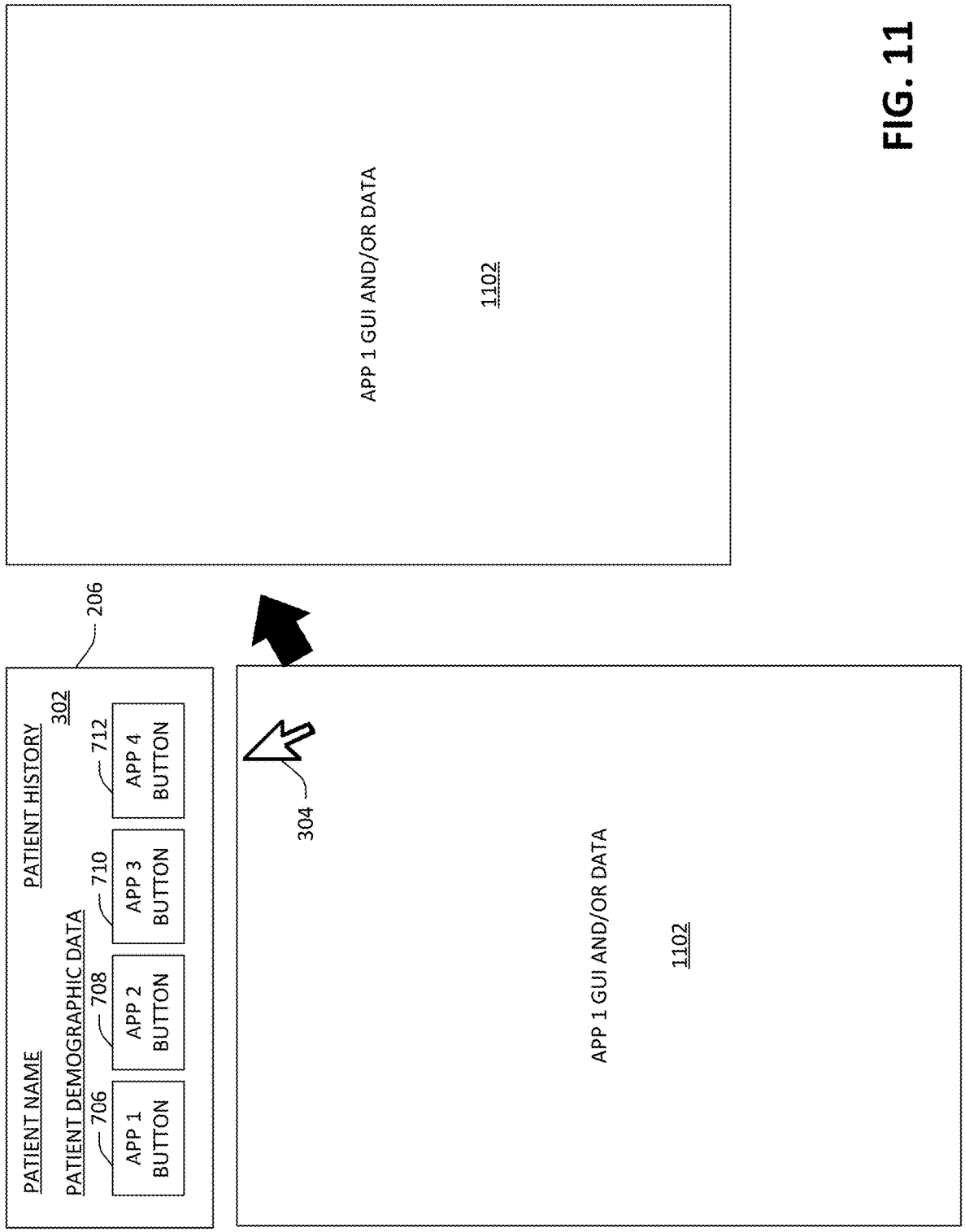

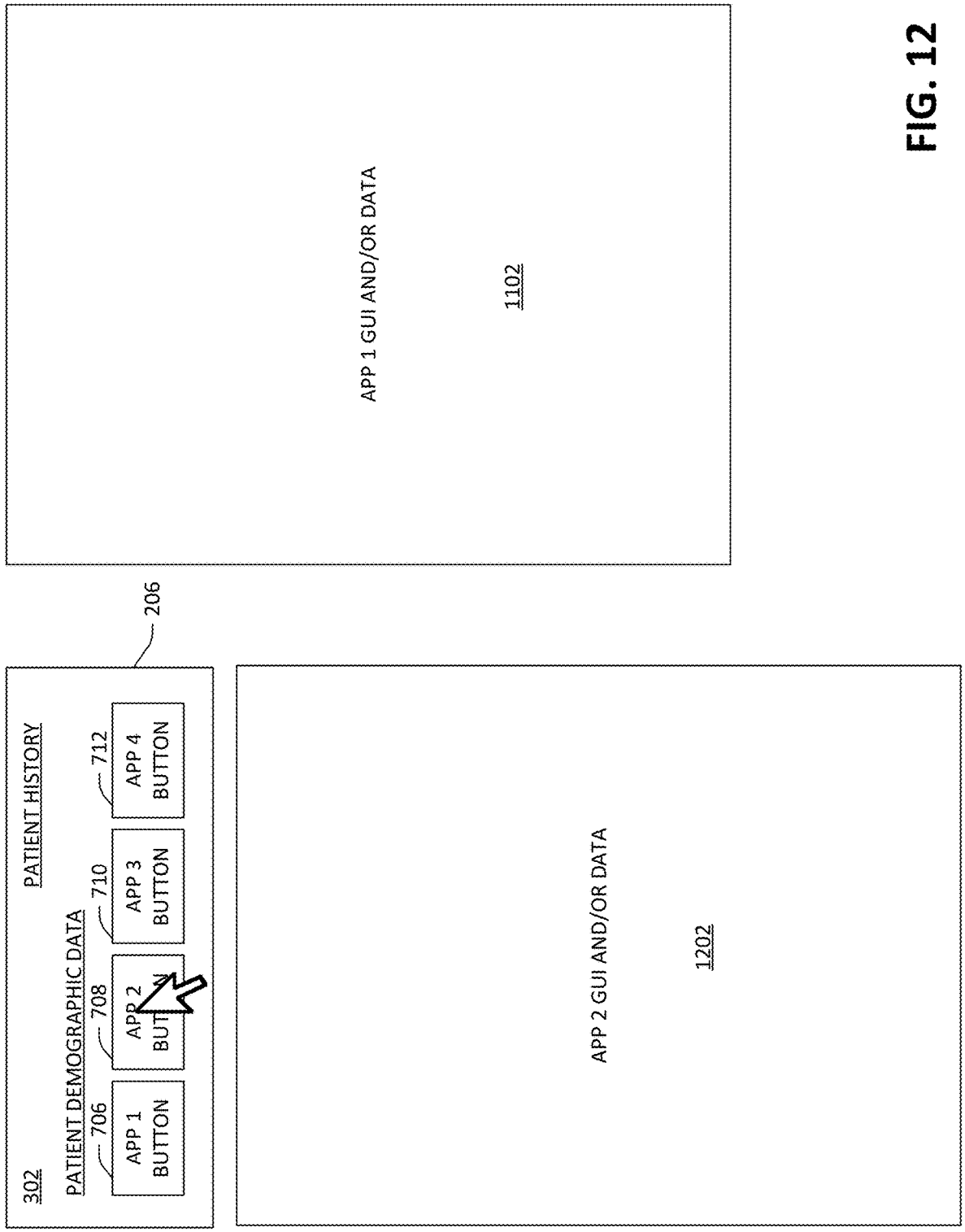

APPLICATION THAT ACTS AS A PLATFORM FOR SUPPLEMENT APPLICATIONS

RELATED APPLICATION

This application claims priority to U.S. Provisional Patent Application No. 62/300,712, filed on Feb. 26, 2016, and entitled "COMPUTING SYSTEM FOR PRESENTING SUPPLEMENTAL CONTENT IN CONTEXT", the entirety of which is incorporated herein by reference.

BACKGROUND

Electronic health record applications (EHRs) are robust applications that are utilized in medical facilities across a variety of aspects of a medical practice. For example, and not by way of limitation, an EHR can include functionality related to patient intake, billing, updating medical records, prescribing medication, tracking care over time, and so forth. Computer-executable applications have been developed to supplement EHRs, wherein such supplement applications cannot be considered EHRs themselves (e.g., the supplement applications do not provide the breadth of features of EHRs, fail to meet regulatory requirements imposed on EHRs by governmental bodies, etc.). A supplement application can, for example, provide data about a patient that supplements the data about the patient in the EHR.

A supplement application can generate the above-referenced supplemental data in the form of events, wherein an event comprises data pertaining to care with respect to a patient at a certain point in time. For example, a supplement application can be configured to generate an event for a patient for each visit to a medical facility (e.g., across several medical facilities). Thus, for instance, when a clinician is provided with a health record for the patient by way of an EHR, the supplement application can provide the clinician with several events corresponding to the patient, thereby providing the clinician with data that is relevant to the care of the patient (e.g., the patient has visited three different medical facilities over the last year). Conventionally, however, supplement applications have not been configured to indicate, in a meaningful way, whether the supplement application has generated a new event since the last use of the supplement application by the clinician. Instead, when the clinician launches the supplement application, the supplement application presents some set number of events to the clinician; thus, the clinician must rely upon memory to ascertain whether the events presented to the clinician have been seen before by the clinician or whether the events include new information not before contemplated by the clinician.

SUMMARY

The following is a brief summary of subject matter that is described in greater detail herein. This summary is not intended to be limiting as to the scope of the claims.

Described herein are various technologies pertaining to computer-executable applications that are well-suited for use in a healthcare environment. More specifically, described herein are various technologies pertaining to a computer-executable supplement application that can be utilized simultaneously with an EHR, where the supplement application is configured to provide a healthcare worker that uses the EHR with contextually relevant information about a patient and/or population of patients.

In an exemplary embodiment, a client computing device can execute both a client EHR and a hub application. The hub application is configured to provide a unified graphical user interface by way of which a plurality of supplement applications can be accessed, and further by way of which information output by the plurality of supplement applications can be presented. The hub application is configured to receive data from the client EHR; thus, for instance, when the client EHR has information about a patient and/or clinician loaded therein, the client EHR can transmit an identifier for the patient and/or an identifier for the clinician to the hub application. A graphical user interface (GUI) of the hub application can include a header field (which may also be referred to as a ribbon), wherein information about the patient and/or clinician is displayed in the header field. For instance, the header field can display the patient name, demographic information about the patient, a patient identifier (such as a medical record number), and so forth. Such information can be received, for instance, from the client EHR. Additionally, the GUI of the hub application can include an applications ribbon, wherein a plurality of selectable buttons that correspond to a respective plurality of supplement applications are displayed. When a button in the plurality of selectable buttons is selected, the hub application causes a GUI for a supplement application that corresponds to the selected button to be presented on the display. Thus, when the supplement application is being executed in the background, selection of the button causes the supplement application to be executed in the foreground. When the supplement application is not being executed, selection of the button causes the supplement application to be executed.

Moreover, the hub application can render badges on the buttons, where a badge on a button can indicate to the clinician that a supplement application corresponding to the button is reporting events that have not been previously viewed by the clinician. Further, the badges can be context-dependent; thus, for instance, a badge on a button can indicate that the supplement application is reporting an event that has yet to be reviewed by the clinician, where the event pertains to the patient whose medical information is loaded in the client EHR. When the clinician hovers over a badge on a button, summary information about one or more events generated by a supplement application that corresponds to the button and indicated by the badge can be presented in a tooltip. Hence, the clinician need not be required to open the supplement application to understand whether the events are relevant to the clinician at a current instant in time.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 9 is yet another exemplary hub application GUI, wherein the hub application GUI is shown in minimized format.

FIG. 10 is yet another exemplary hub application GUI, wherein a flyout includes selectable buttons that are representative of types of supplement applications.

FIG. 11 illustrates undocking of a GUI for a supplement application from a hub application GUI.

FIG. 12 illustrates multiple GUIs of supplement applications being presented concurrently with a hub application GUI.

DETAILED DESCRIPTION

Figure 1:
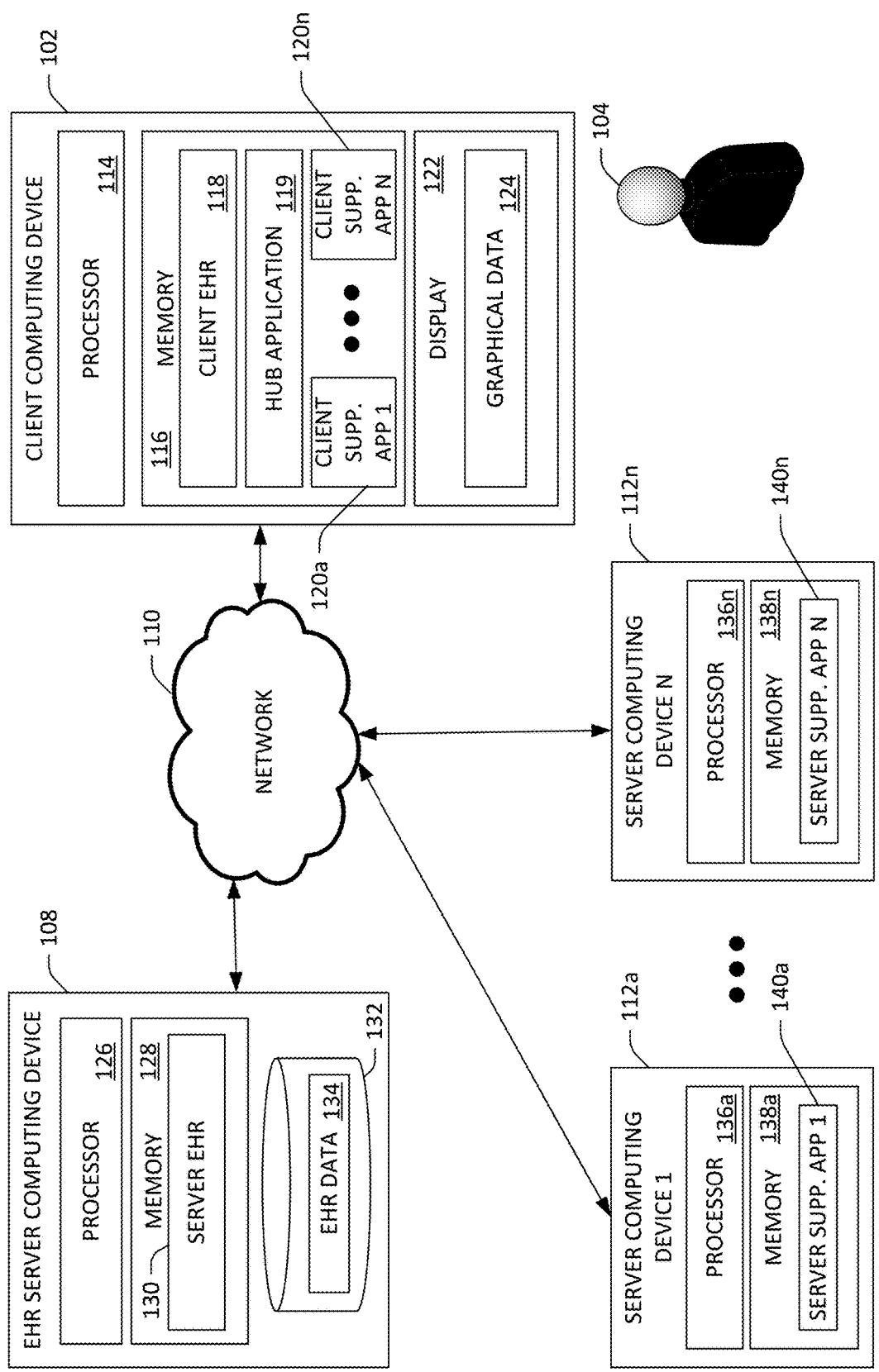
FIG. 1 is a functional block diagram of an exemplary system that facilitates presentment of supplemental data to a user of an EHR.

Various technologies pertaining to supplement applications that are configured to present contextually relevant data to a healthcare worker are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, the features described herein pertain to technologies for displaying graphical data to a clinician that is relevant to a current context of the clinician. More specifically, a clinician can employ an electronic health record application (EHR), wherein the EHR is a distributed application that includes a client-side application (client EHR) executing on a client computing device and a server-side application (server EHR) executing on a server computing device, and further wherein the client EHR and the server EHR are in communication with one another. For instance, the client EHR can receive authentication data from a clinician, and can further receive data that is indicative of an identity of a patient. The client EHR can transmit such data to the server EHR, which can authenticate the clinician and acquire information about the patient from a database (where the clinician is authorized to view the information). The server EHR can transmit this information to the client EHR, wherein the client EHR presents such information to the clinician.

The client computing device can further execute a hub application that is in communication with the client EHR. The hub application is configured to provide a graphical user interface (GUI), wherein the GUI of the hub application presents information that is relevant to the current context of the client EHR. Thus, in an example, the hub application can present data that is relevant to a patient whose record is being presented to the clinician by way of the client EHR. The GUI of the hub interface also includes a ribbon, wherein the ribbon comprises a plurality of buttons, and further wherein each button corresponds to a respective supplement application.

A supplement application is one that is in communication with the client EHR, and is configured to present data to an end user (e.g., a clinician) that supplements what is being displayed to the end user by way of the client EHR. Hence, for example, if the client EHR is presenting information about a patient to a clinician (e.g., such as a patient record), the client EHR can provide the supplement application with data that is indicative of an identity of the patient. The supplement application may then be configured to retrieve population data that is relevant to the patient, wherein such data can be presented to the clinician by way of the supplement application (e.g., simultaneously with data that is presented to the end user by way of the client EHR). Additionally, similarly to the EHR, a supplement application is a distributed application that includes a client supplement application (executed on the client computing device) and a server supplement application (executed on a server computing device). The client supplement application is configured to present data to an end user and receive input from the end user, while the server supplement application is configured to perform backend processing based upon data received by the client supplement application from the client EHR.

In contrast to conventional approaches, the hub application is configured to act as a platform for several supplement applications (possibly of different application types). Thus, an operator of the computing system can access several supplement applications by way of the hub application. Further, the hub application can be configured to render badges on buttons that are representative of supplement applications, wherein a badge on a button indicates that the supplement application represented by the button has created at least one event that has yet to be reviewed by the clinician, wherein the at least one event is relevant to the current context of the client EHR. For instance, a badge on a button can indicate that a supplement application corresponding to the badge has generated three events that are relevant to a patient, wherein the client EHR presents health data about the patient. Therefore, the clinician can quickly understand which supplement applications have updates that are relevant to the current context of the client EHR that have yet to be reviewed by the clinician, and can further understand how many updates (events) each supplement application has produced that have yet to be reviewed by the clinician.

Now referring to FIG. 1, an exemplary system 100 that facilitates presenting contextually-relevant supplemental data simultaneously with data presented by way of a client EHR is illustrated. The system 100 includes a client computing device 102 that is operated by a healthcare worker 104 (e.g., a clinician, a billing specialist, etc.). The healthcare worker 104 may be utilizing the client computing device 102 in connection with providing care to a patient (not shown). The patient may be in close proximity to the healthcare worker 104, or the healthcare worker may be providing care to the patient remotely. The client computing device 102 operated by the healthcare worker 104 may be any suitable type of client computing device, including a desktop computing device, a laptop computing device, a mobile telephone, a tablet computing device, a wearable computing device, or the like.

The system 100 further includes an EHR server computing device 108 that is in communication with the client computing device 102 by way of a suitable network 110, such as the Internet, an intranet, or the like. The system 100 additionally includes a plurality of server computing devices 112a-112n that are in communication with the client computing device 102 by way of the network 110. While the system 100 is illustrated as including numerous server computing devices, it is to be understood that actions undertaken by several server computing devices may be performed by a single server computing device. Further, actions described as being performed by a single server computing device may be performed by multiple server computing devices. Moreover, while the client computing device 102 is depicted as being in communication with the server computing devices 108 and 112a-112n by way of the network 110, it is to be understood that the client computing device 102 may be in communication with the server computing devices 108 and 112a-112n over different networks. Further, the EHR server computing device 108 can be an enterprise device, whose operation is controlled by a healthcare enterprise. In another example, the EHR server computing device 108 can be a cloud-based computing device, where maintenance and operation of the EHR server computing device 108 is handled by a company that provides an EHR for use by a healthcare enterprise. Typically, the server computing devices 112a-112n are cloud-based computing devices, where maintenance and operation of the server computing devices 112a-112n is under the control of entities that are separate from the healthcare enterprise.

The client computing device 102 includes a processor 114 and memory 116. The memory 116 stores instructions that are executed by the processor 114. More specifically, the memory 116 includes a client EHR 118, a hub application 119, and a plurality of client supplement applications 120a-120n. As will be described in greater detail herein, each client supplement application in the client supplement applications 120a-120n is configured to acquire data that is contextually relevant to information being presented to the healthcare worker 104 by way of the client EHR 118, and is further configured to present the contextually relevant data upon request. The client computing device 102 further comprises a display 122, which is configured to present graphical data 124 to the healthcare worker 104. The graphical data 124 may include data presented by way of the client EHR 118, a GUI of the hub application 119, and data presented by way of one or more of the client supplement applications 120a-120n. While the display 122 is depicted as being integral to the client computing device 102, it is to be understood that the display 122 may be externally coupled to the client computing device 102 or may be a projected display.

The EHR server computing device 108 comprises a processor 126 and memory 128 that stores instructions that are executed by the processor 126. As shown in FIG. 1, the memory 128 includes a server EHR 130. The EHR server computing device 108 further includes a data store 132 that comprises EHR data 134. In operation, the healthcare worker 104 can interact with the client EHR 118 executing on the client computing device 102. This interaction causes the client EHR 118 to transmit data to the server EHR 130 executing on the EHR server computing device 108. Content of the data transmitted to the server EHR 130 can include, for instance, data that identifies the healthcare worker 104 and data that identifies the patient 106, amongst other data. Responsive to receipt of such data, the server EHR 130 can construct a query based upon the data and search over the EHR data 134 in the data store 132 based upon the query, thereby obtaining search results. The EHR data 134 can include any suitable data that is used in connection with provision of care to the patient 106, including an electronic patient record for the patient 106. The server EHR 130 then causes the EHR server computing device 108 to transmit the search results to the client computing device 102, whereupon the search results are provided to the client EHR 118. The client EHR 118 subsequently causes at least a portion of the search results to be presented in the graphical data 124 on the display 122 of the client computing device 102.

In a more specific example, the healthcare worker 104, through utilization of a human machine interface (HMI), can interact with the client EHR 118 by providing input pertaining to the patient (referenced above). The client EHR 118 transmits this information to the server EHR 130, which can construct a query based upon the data and search over the EHR data 134 using the query. The server EHR 130 can then return corresponding search results to the client EHR 118. The client EHR 118 causes at least a portion of the search results (e.g., a portion of an electronic medical record (EMR) of the patient) to be displayed on the display 122 (e.g., as part of the graphical data 124).

The server computing devices 112a-n include respective processors 136a-n and respective memory 138a-n, wherein the memory 138a-n store instructions that are executed by the processors 136a-n. As shown, the memory 138a-n include respective server supplement applications 140a-n, wherein the server supplement applications 140a-n respectively correspond to the client supplement applications 120a-n. At least one of the server supplement applications 140a-n can be configured to search over population data in a data store (not shown), where the population data can be acquired from several different data sources. For instance, the data sources may include another EHR application, web pages, a healthcare information exchange (HIE), etc. It can therefore be ascertained that the population data can include population health data retrieved and aggregated from a myriad of different data sources, wherein at least some of the population data pertains to the patient and is not duplicative as to data about the patient in the EHR data 134.

Operation of the hub application 119, the client supplement applications 120a-120n, and the server supplement applications 140a-140n is now described. The hub application 119 operates as a platform for the supplement applications 120-120n, such that the supplement applications 120-120n can be launched by way of the hub application 119, and further wherein the hub application 119 can present data that indicates that the supplement applications 120a-120n have produced one or more events related to the current context of the client EHR 118. Further, in an exemplary embodiment, the hub application 119 can communicate with the server supplement applications 140a-n directly. In another exemplary embodiment, the hub application 119 can communicate with the server supplement applications 140a-n indirectly (e.g., by way of the client supplement applications 120a-120).

The client EHR 118 is operated by the healthcare worker 104, such that the context of the client EHR 118 changes. For instance, the client EHR 118 can receive input from the healthcare worker 104 pertaining to a particular patient, and the client EHR 118 can direct such input to the server EHR 130. The server EHR 130 can execute a query over the EHR data 134 based upon the input received from the client EHR 118, and can direct the search results to the client EHR 118. These search results can include data that identifies the patient, demographics about the patient, and the like. The client EHR 118 can cause at least a portion of the search results to be presented on the display 122 of the client computing device 102; thus, the context of the client EHR 118 has changed.

As indicated above, the client EHR 118 is in communication with the hub application 119, and is further optionally in communication with client supplement applications 120a-n. In an exemplary embodiment, the client EHR 118 can transmit data that is indicative of the current context of the client EHR 118 to the hub application 119. Responsive to receiving the data that is indicative of the current context of the client EHR 118, the hub application 119 can update the GUI of the hub application 119 to depict, for instance, the name of the patient whose information is presented by way of the client EHR 118, demographic information about the patient (e.g., age, gender, geographic location), and so forth. Further, the client supplement applications 120a-120n can receive the data that is indicative of the current context of the client EHR 118. In an example, the hub application 119 can provide the client supplement applications 120a-120n with the data that is indicative of the current context of the client EHR 118 in response to receipt of such data from the client EHR 118. In another example, the client supplement applications 120a-120n can be configured to receive the data that is indicative of the context of the client EHR 118 directly from the client EHR 118.

The client supplement applications 120a-120n, in response to receiving the data that is indicative of the current context of the client EHR 118, can transmit such data to their respective server supplement applications 140a-140n. A server supplement application, upon receipt of this data, performs a computing operation in accordance with the intended function of the server supplement application. For instance, the server supplement application 140a can search population data pertaining to the patient to identify diagnoses of a condition of the patient in other patients in a certain geographic region. Further, the server supplement application 140n can search population data pertaining to the patient to identify new prescriptions for the patient (prescribed by healthcare facilities that are different from the healthcare facility of the clinician 104). From the foregoing examples, it can be ascertained that each server supplement application in the server supplement applications 140a-140n can generate events, wherein an event is a discrete set of information produced by a supplement application. With reference to the examples above, an event produced by the server supplement application 140a can be individual diagnoses of other patients; an event produced by the server supplement application 140n can be an individual prescription for the patient, etc.

The server supplement applications 140a-140n can also retain state information pertaining to events produced by the server supplement applications 140a-140n for each context of the client EHR 118. Put differently, the server supplement applications 140a-140n can, for each context of the client EHR 118, determine whether there are any events produced by the server supplement applications 140a-140n that have yet to be reviewed by the clinician 104. Events that have yet to be reviewed by the clinician 104 are referred to herein as updates. In a specific, non-limiting example, at least one of the supplement applications 140a-140n can retain state for the context pair (patient ID, clinician ID)—thus, the supplement application 140a can have knowledge of the events produced by the supplement application 140a that the clinician 104 has previously reviewed, and the supplement application 140a can further have knowledge of what new events (updates) that have been produced by the supplement application 140a that the clinician has not reviewed.

The server supplement applications 140a-140n can then direct update information to the client supplement applications 120a-120n, respectively. The update information can include a number of updates that have been generated by the server supplement applications 140a-140n as well as summaries of such updates. The server supplement applications 140a-140n can utilize any suitable business logic to define events/updates, and to ascertain what information to provide to the client supplement applications 120a-120n. The client supplement applications 120a-120n can then provide at least a portion of the update information to the hub application 119, and the hub application 119 can cause such information to be presented on the display 122.

While FIG. 1 depicts a specific architecture for the system 100, and data has been described as being directed from the client EHR 118 to the hub application 119, from the hub application 119 to the client supplement applications 120a-120n, from the client supplement applications 120a-120n to the server supplement applications 140a-140n, from the server supplement applications 140a-140n back to the client supplement applications 120a-120n, and from the client supplement applications 120a-120n to the hub application, other architectures and data flows are also contemplated. For example, the hub application 119 may be a distributed application, such that it has a server-side component. In an exemplary embodiment, data can flow from the hub application 119 to its server-side counterpart, and from such counterpart to the server supplement applications 140a-140n. In another example, the hub application 119 may communicate directly with the server supplement applications 140a-140n, such that the hub application 119 acts as a broker between the client supplement applications 120a-120n and the server supplement applications 140a-140n. Other architectures and data flows are also contemplated.

Figure 2:
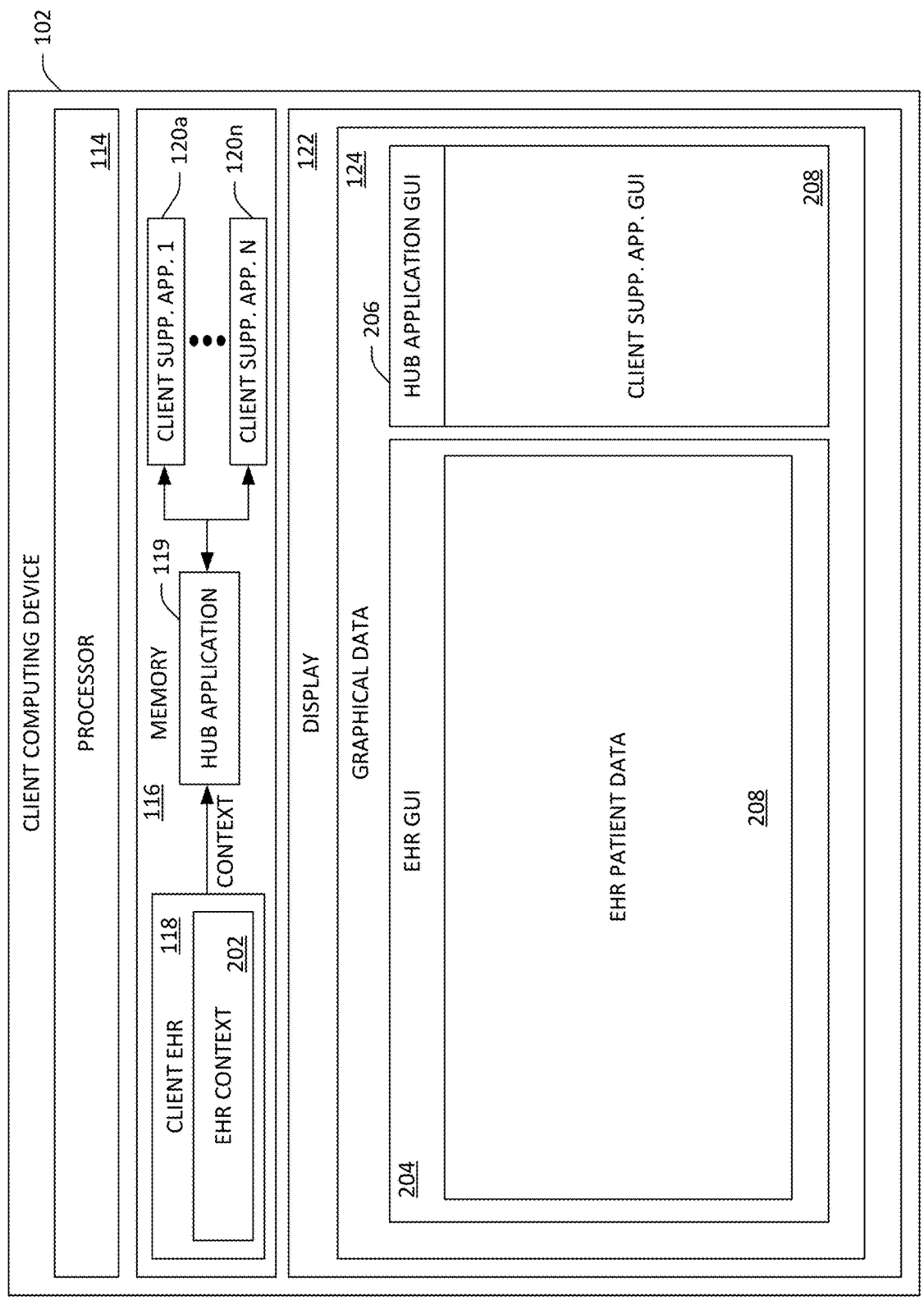
FIG. 2 depicts an exemplary client computing device.

With reference now to FIG. 2, a functional block diagram of the client computing device 102 is illustrated. As indicated previously, the client EHR 118 is loaded in the memory 116 and is executed by the processor 114. The client EHR 118 has an EHR context 202, where the EHR context 202 is indicative of a current state of the client EHR 118, including an identity of the clinician 104 utilizing the client EHR 118, an identity of the patient (e.g., when data about the patient is loaded into the client EHR 118), etc. The processor 114, when executing the client EHR 118, causes a client EHR GUI 204 to be included in the graphical data 124 on the display 122. In this example, the client EHR GUI 204 comprises EHR patient data (data about the patient). The client EHR 118 can provide the EHR context 202 to the hub application 119, which in turn can provide the EHR context 202 to the client supplement applications 120a-120n, as described above.

The processor 114, when executing the hub application 119, causes a hub application GUI 206 corresponding to the hub application 119 to be presented on the display 122 as a part of the graphical data 124. As will be described in greater detail below, the hub application GUI 206 can include several buttons, where the buttons are respectively representative of the supplement applications (the client supplement applications 120a-120n and the server supplement applications 140a-140n). When the healthcare worker 104 selects a button in the hub application GUI 206, the processor 114 can present a client supplement application GUI 208 for the supplement application represented by the selected button. The client supplement application GUI 208 can be presented to appear integrated with the hub application GUI 206. Further, the buttons can have badges rendered thereon, wherein a badge on a button can be indicative of a number of updates, with respect to the EHR context 202, that are available from a supplement application represented by the button, where the updates are available for review by the healthcare worker 104.

Figure 3:
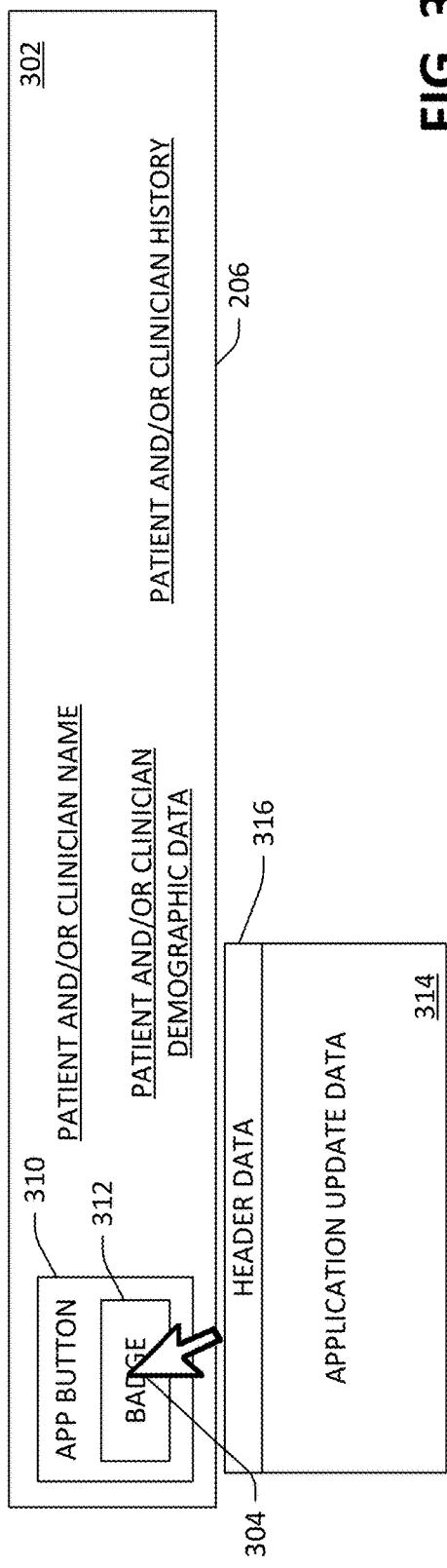
FIG. 3 depicts an exemplary hub application GUI.

With reference to FIG. 3, an exemplary illustration of the hub application GUI 206 is illustrated. In the example shown in FIG. 3, the hub application GUI 206 includes a ribbon 302. The ribbon 302 includes at least a portion of the EHR context 202. For instance, the ribbon 302 can include the name of the patient, the name of the healthcare worker 104, patient and/or clinician demographic data (date of birth, gender, etc.), and optionally, patient and/or clinician history (time of last encounter). The patient and/or clinician name can further include a unique identifier for the patient and/or clinician in the client EHR 118.

The ribbon 302 may further include a selectable application button 310 that is representative of one of the supplement applications 120a-120n. In this example, the ribbon 302 further includes a badge 312 rendered in the application button 310. As described previously, the badge 312 can identify a number of updates reported by the supplement application represented by the application button 310. For instance, the badge 312 may include an integer. Hovering a cursor 304 over the badge 312 (or otherwise selecting the badge 312) may cause a tooltip 314 to be rendered on the display 122. The tooltip 314 can include update data reported by the supplement application that is represented by the application button 310. In a non-limiting example, the tooltip 314 may include header data 316, which can identify a total number of updates reported by the supplement application and a time period for which updates are displayed. In another example, the header data 316 may include first day of admission data. For instance, if a patient has been admitted to the hospital within a certain time period, the header data 316 can display admission time with the following text: the patient has been admitted today at time.

Again, the application update data 314 can include any suitable update data reported by the supplement application represented by the button 310. In non-limiting examples, the application update data for each update can include the title of the update, as well as the date and content of the update. The title of the update can indicate a type of the update and the number of updates per type. For instance, if the supplement application tracks patient encounters, the title of the update can indicate that is it update 1 of 3, for example. The supplement application can be configured with any suitable logic to determine when and how the badge 312 is displayed on the button 310. As described previously, the badging functionality is used to visually indicate to the healthcare worker 104 when there is recent clinical information that is available by way of the supplement application, but may be unavailable in the client EHR 118. Considerations when configuring the supplement application to report updates for badging are as follows: 1) the time period for badging (e.g., how much time prior to the current time does the supplement application check for updates) and whether badging is enabled or disabled. When determining whether to surface updates, the supplement application can perform the following acts: 1) the supplement application can identify updates, by ascertaining whether events of the supplement application already exist in the EHR. The remaining events are then filtered, and the supplement application checks as to whether there are events that are semantically identical or similar to events existing in the EHR—these similar events are also filtered out. Subsequently, the supplement application checks for remaining events based on a configurable timeframe that is used for clinical domains. If there is at least one event that remains after all the filtering, the supplement application surfaces the update, and the hub application 119 displays the badge 312 on the button 310 in the hosted application GUI 206. The supplement application may then cache this result.

Figure 4:
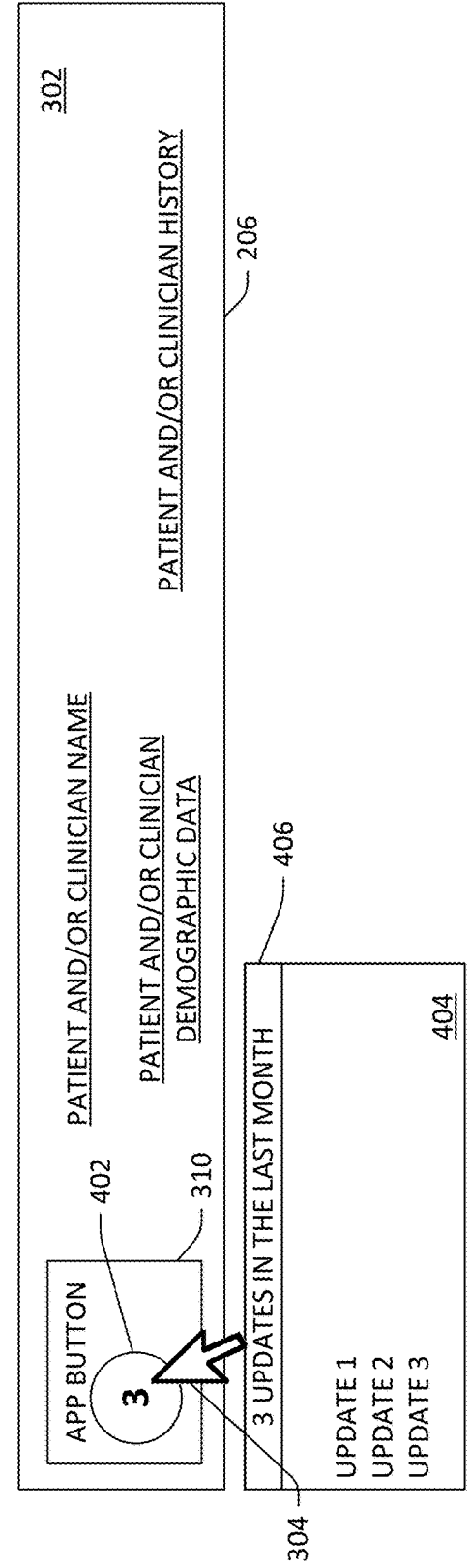
FIG. 4 depicts another exemplary hub application GUI.

Now referring to FIG. 4, another exemplary depiction of the hub application GUI 206 is illustrated. The application button 310 has a badge 402 rendered thereon, indicating that a supplement application (represented by the application button 310) is reporting updates. In the example shown in FIG. 4, the supplement application is reporting three updates, such that the badge 302 includes the integer "3". The healthcare worker 104 can hover the cursor 304 over the badge 402, causing a tooltip 404 be presented. A header 406 of the tooltip 404 indicates that the supplement application is reporting three updates in the last month (which presumably are unable to be viewed by the healthcare worker 104 in the EHR). The tooltip 404 also includes data about the three updates.

Figure 5:
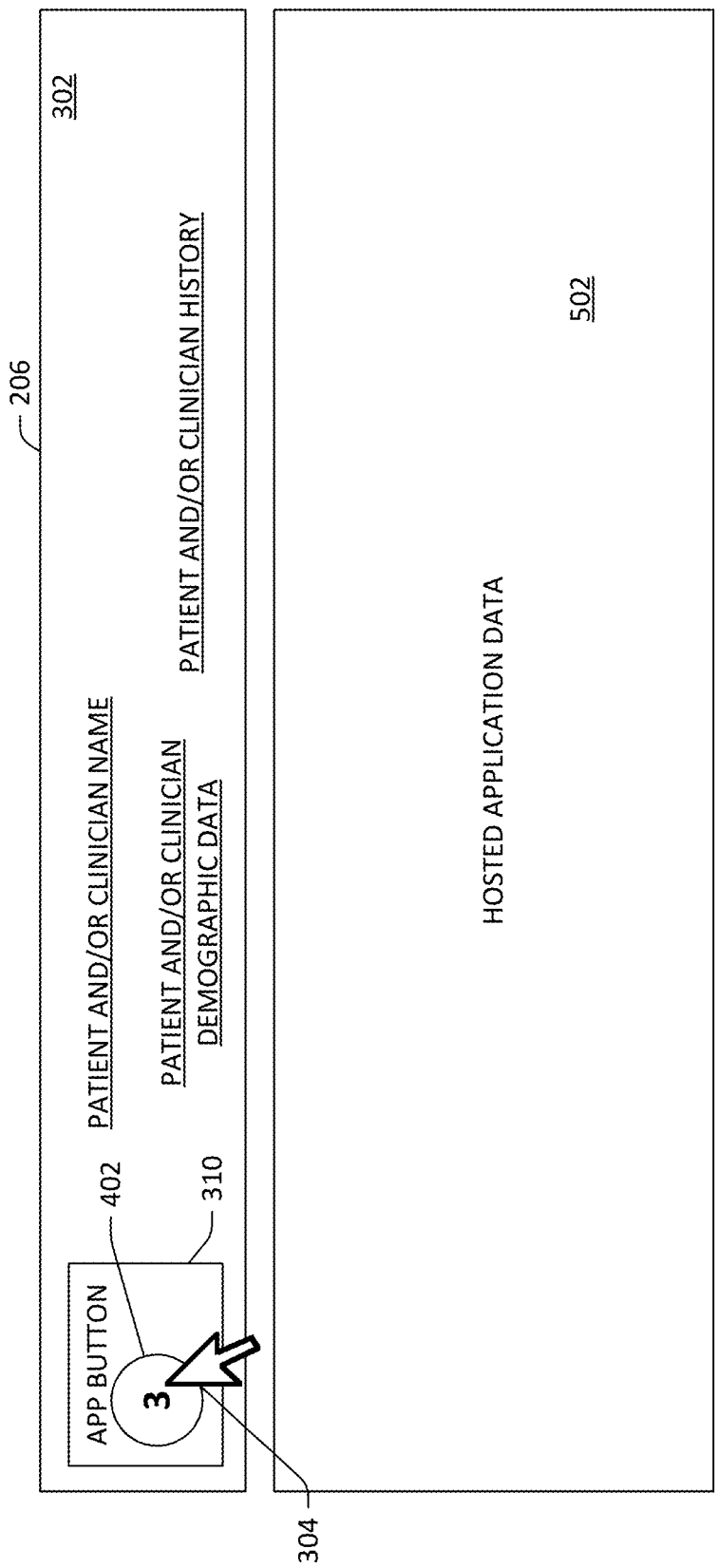
FIG. 5 illustrates yet another exemplary hub application GUI.

With reference now to FIG. 5, another exemplary depiction of the hub application GUI 206 is presented. Here, rather than the cursor 304 being hovered over the badge 402, the cursor 304 is used to select the application button 310. Selection of the application button 310 causes a GUI for the (client) supplement application represented by the application button 310 to be shown on the display 122. This results in supplement application data being presented in a window 502 that is separate from the ribbon 302. Alternatively, the window 502 can be presented in a pulldown from the ribbon 302. In an example, the window 502 can be a portion of a GUI that corresponds to the hub application 119. In another example, the window can be included in a GUI that is unique to the supplement application.

Figure 6:
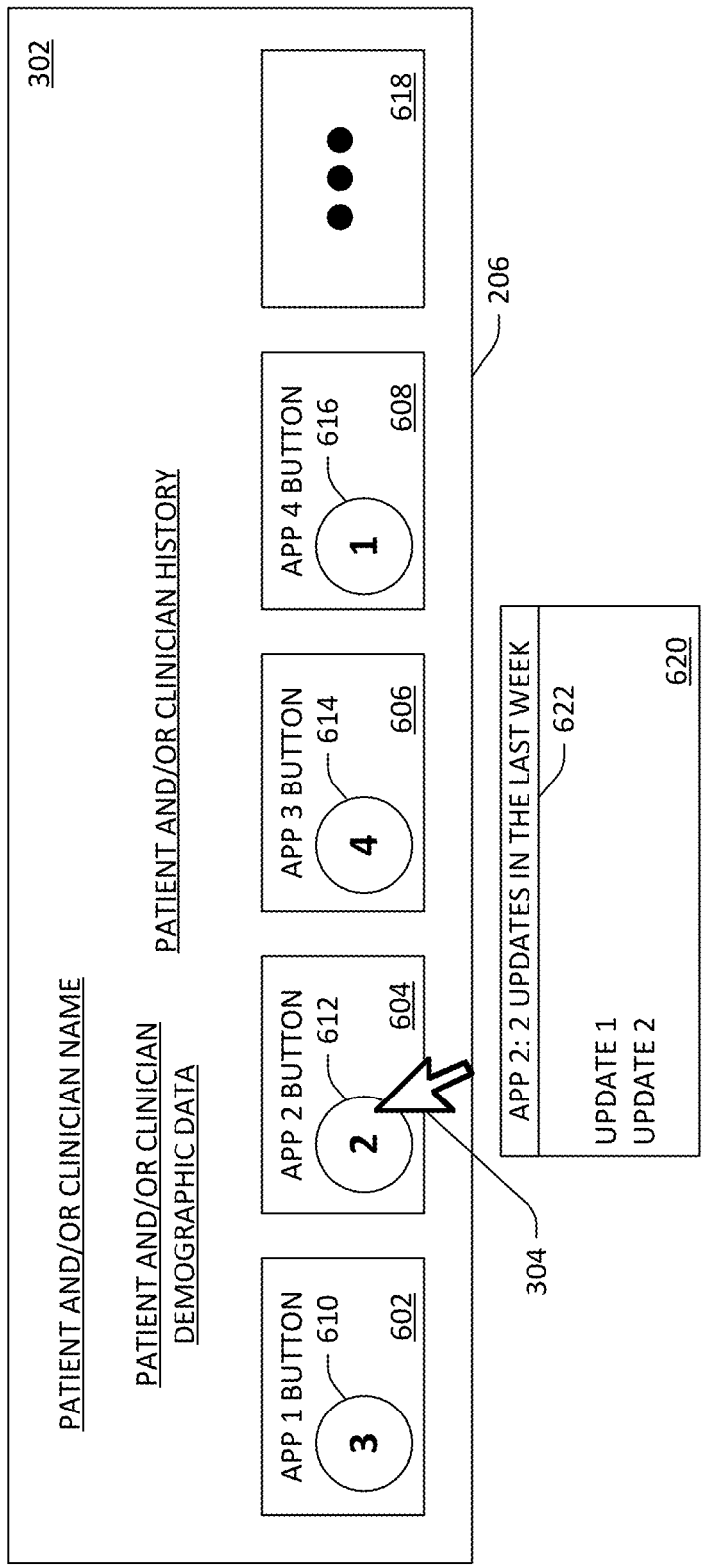
FIG. 6 illustrates still yet another exemplary hub application GUI.

With reference now to FIG. 6, another exemplary depiction of the hub application GUI 206 is illustrated. The hub application GUI 206 includes the ribbon 302. As indicated previously, the hub application 119 may act as a platform for several supplement applications. Accordingly, the ribbon 302 may include a plurality of buttons 602-608 that respectively represent the plurality of supplement applications. As noted above, each of these applications may report updates to the hub application 119. For instance, the first application button 602 includes a badge 610 that indicates that the first supplement application has reported three updates. Similarly, the second application button 604 includes a badge 612 that indicates that a second supplement application has reported two updates. If a supplement application does not report updates, then the button that represents the supplement application will not include a badge. The buttons 606 and 608 include badges 614 and 616, respectively, indicating that supplement applications represented by the buttons 606 and 608 reported updates for the EHR context 202.

The ribbon 302 may optionally include a graphical button 618 that indicates that the hub application 119 interfaces with more applications than what are represented in the ribbon 302. For instance, selection of the icon 618 can cause a fly-out or pulldown to be presented that includes more selectable buttons that are representative of supplement applications that interface with the hub application 119. The buttons 602-608 can be selected for inclusion in the ribbon 302 based upon any suitable metric, such as recency of use, frequency of use, number of updates, or the like. The cursor 304 is depicted as being hovered over the badge 612, resulting in a tooltip 620 being rendered on the display 122. A header 622 of the tooltip 620 indicates that the supplement application represented by the second application button 604 has reported two updates in the past week. The tooltip 620 further includes information about both of such updates.

Figure 7:
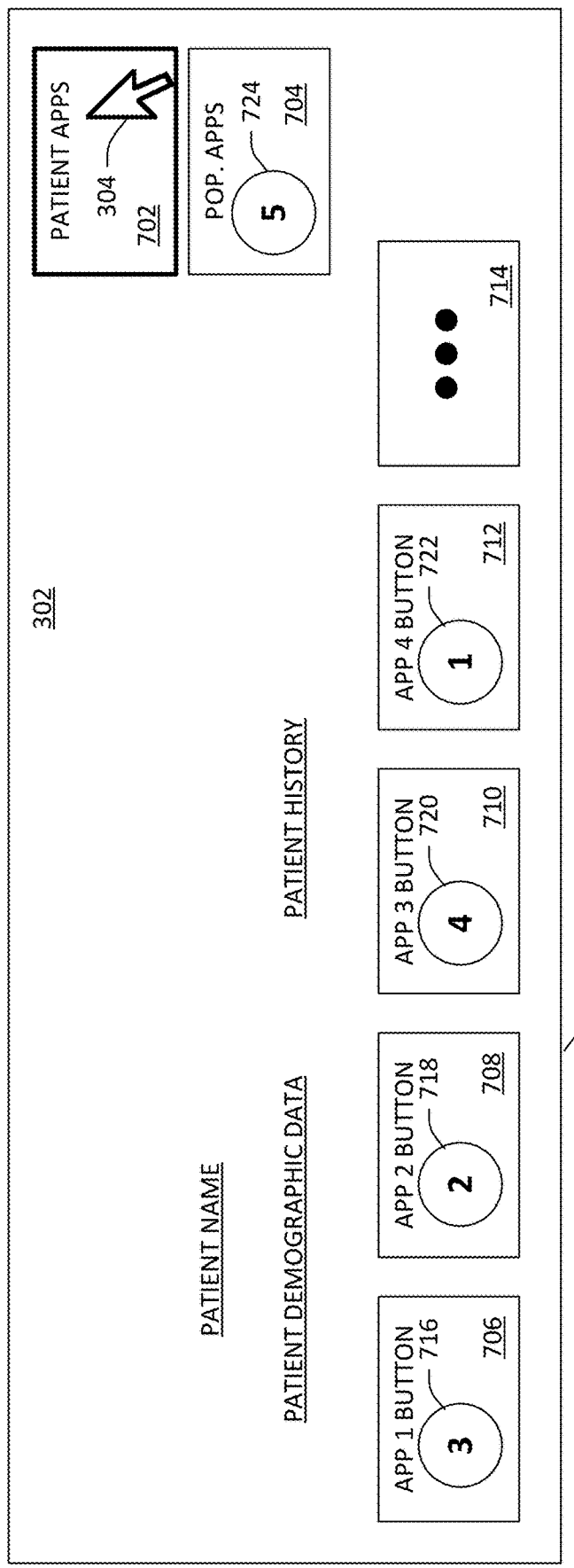
FIG. 7 depicts another exemplary hub application GUI, wherein the hub application acts as a platform for a plurality of supplement applications of different types.

Now referring to FIG. 7, yet another exemplary depiction of the hub application GUI 206 is illustrated. The GUI 206 includes the ribbon 302. In this example, the ribbon 302 includes a first button 702 and a second button 704. The first button 702 identifies a first category of application that interfaces with the hub application 119. More specifically, the first button 702 indicates that patient-centric applications interface with the hub application 119. When the first button 702 is selected (e.g., through use of the cursor 304), the ribbon 302 is rendered to include a plurality of buttons 706-712 that are representative of patient-centric applications that interface with the hub application 120. Further, the ribbon 302 is updated to identify the patient name, patient demographic data, patient history, and other information about the patient 106 (wherein the client EHR 118 has data about the patient loaded therein and presented in the EHR GUI 204). The ribbon 302 further includes a button 714, which when selected, acts as described with respect to the button 618 (FIG. 6).

The buttons 706-712 are shown as including respective badges 716-722. Further, the second button 704 (which indicates that the hub application 119 interfaces with population-centric applications) has a badge 724 rendered thereon, wherein the badge 724 indicates that at least one population-centric application is reporting an update. In an example, the badge 724 can identify an aggregate number of updates reported by population-centric applications that interface with the hub application 119. In another example, the badge 724 can indicate a number of updates reported by the most frequently used population-centric application that interfaces with the hub application 119. In yet another example, the badge 724 can represent a number of updates reported by a population-centric application that interfaces with the hub application 119 that is reporting the highest number of updates.

Figure 8:
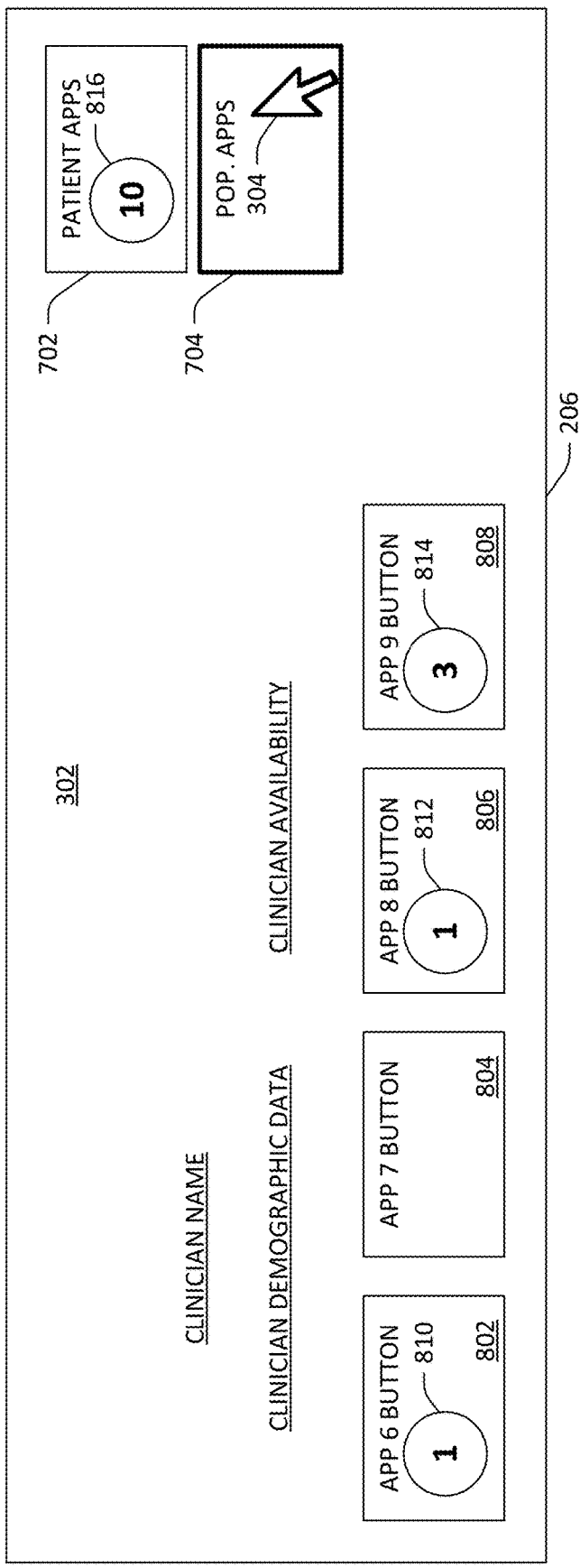
FIG. 8 depicts yet another exemplary hub application GUI, where an operator of a computing device is able to toggle between supplement applications of different types.

Now referring to FIG. 8, yet another exemplary depiction of the hub application GUI 206 is illustrated. The GUI 206 includes the ribbon 302, the first button 702, and the second button 704. In the exemplary GUI 206 shown in FIG. 8, the second button 704 (representative of the category of population-centric applications that interface with the hub application 119) is selected through use of the cursor 304. Selection of the second button 704 can cause the ribbon 302 to include the name of the healthcare worker 104, demographic data about the healthcare worker 104, and availability of the healthcare worker 104 (e.g., in a manner similar to instant messaging). For instance, the ribbon 302 can indicate that the healthcare worker 104 is "available", "busy", "in a meeting", "on a call", etc. Selection of the second button 704 causes the ribbon 302 to have rendered therein a plurality of buttons 802-808 that are respectively representative of population-centric applications that are accessible by way of the hub application 119. The buttons 802, 806, and 808 have badges 810, 812, and 814 respectively rendered thereon, indicating that the population-centric applications represented by the buttons 802, 806, and, 808 have reported updates.

The population-centric application represented by the button 804 has not reported updates (e.g., the healthcare worker 104 has seen each event reported by such population-centric application), and thus the button 804 has no badge rendered thereon. The first button 702 has a badge 816 rendered thereon, which indicates that at least one patient-centric application that interfaces with the hub application 119 has reported an update. As indicated previously, the badge 816 can indicate an aggregate number of updates reported by patient-centric applications that interface with the hub application 119, can indicate a number of updates reported by a most popular patient-centric application that interfaces with the hub application 119 (e.g., where the most popular is the one used most by the healthcare worker 104), can indicate a number of updates reported by a patient-centric application that is reporting a highest number of updates, etc. In summary, then, GUIs for the hub application 119 allow the healthcare worker 104 to toggle between buttons that are representative of patient-centric applications and buttons that are representative of population-centric applications, wherein the hub application 119 interfaces with both patient-centric applications and population-centric applications.

Turning now to FIG. 9, still yet another exemplary depiction of the hub application GUI 206 is illustrated. In the GUI 206 shown in FIG. 9, the ribbon 302 is minimized (e.g., when space on the display 122 is at a premium). The ribbon 302 is depicted as including the buttons 706-712 (and associated badges 716-722), but is shown as not depicting the patient name, patient demographic data, patient history, the first button 702, or the second button 704. The ribbon 302 includes a pulldown button 902 which is selectable, for example, through utilization of the cursor 304. While not shown, the GUI 700 (FIG. 7) can include an icon that, when selected, causes the ribbon 302 to be minimized. Alternatively, the ribbon 302 can be automatically minimized based upon available display screen real estate.

FIG. 10 is another exemplary hub application GUI 206, which includes a fly-out 1002 that is presented upon user selection of the button 902. The fly-out 1002 includes the first button 702 and the second button 704. In this example, the first button 702 can be highlighted and/or aligned with the buttons 706-712 to indicate to the healthcare worker 104 that the buttons 706-712 shown in the ribbon 302 represent patient-centric applications that interface with the hub application 119 (rather than population-centric applications). The healthcare worker 104 may select the second button 704 through utilization of the cursor 304, which would cause the buttons 802-808 to be rendered in the (minimized) ribbon 302. The fly-out 1002 further includes a pulldown button 1004 that, when selected, can optionally display additional buttons that are representative of other patient-centric applications that interface with the hub application 119.

With respect to the badges described above, a badge can be cleared, for example, responsive to detecting that the cursor 304 has been detected as being hovered over the badge. In another example, the badge can be cleared upon the application reporting the update being opened or launched. In yet another example, badges can be periodically cleared and/or updated.

With reference now to FIG. 11, undocking of an application GUI from the ribbon 302 is illustrated. In the example shown in FIG. 11, the healthcare worker 104 can employ the cursor 304 to select the button 706. This can cause a graphical user interface 1102 for the application represented by the button 706 to be displayed immediately beneath the ribbon 302. Conventionally, the healthcare worker 104 is unable to cause more than one GUI for a supplement application to be presented at once. In this example, however, the healthcare worker 104 can utilize the cursor 304 to select the application GUI 1102 and drag the application GUI 1102 to a different location on the display 122. After the application GUI 1102 has been dragged to the different location, at least a portion of an area beneath the ribbon 302 will be misaligned with the application GUI 1102.

Now referring to FIG. 12, it can be ascertained that the cursor 304 is employed to select the button 708, which causes a second application GUI 1202 to be displayed immediately beneath the ribbon 302. Meanwhile, the first application GUI 1102 remains in that position where it was dragged by the healthcare worker 104 on the display 122. Accordingly, the healthcare worker 104 can simultaneously review data reported by the application represented by the first application button 706 and the application represented by the second application button 708.

Figure 13:
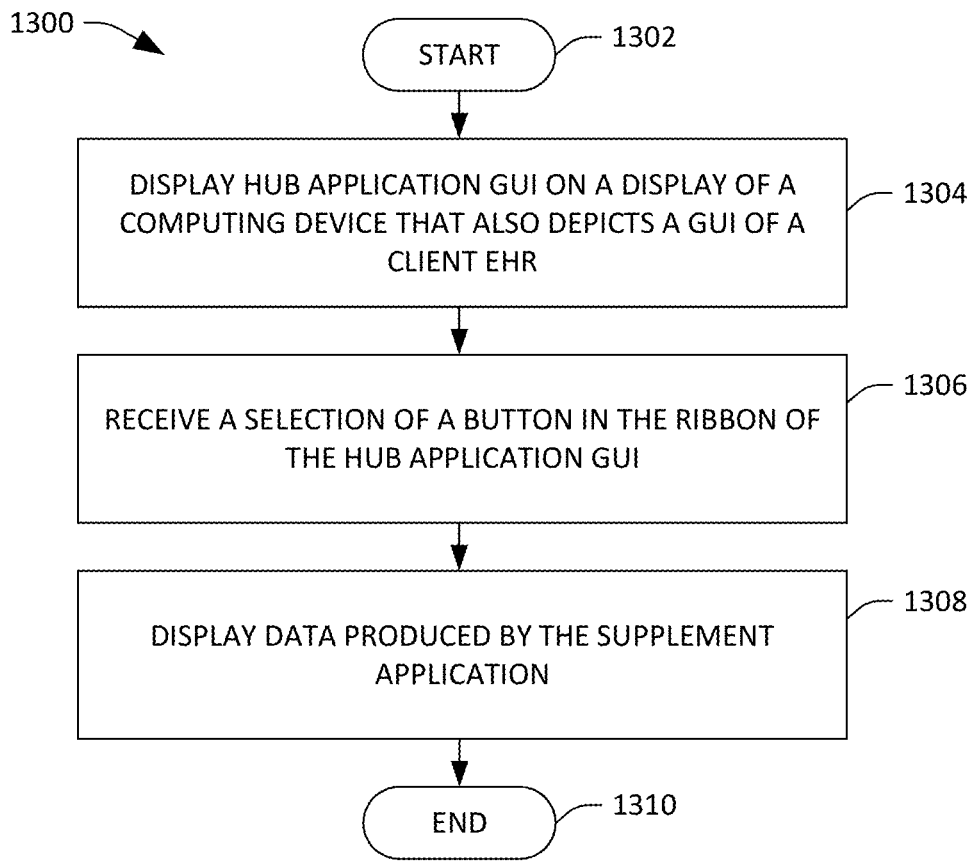
FIG. 13 is a flow diagram illustrating an exemplary methodology for displaying an update from a supplement application by way of a GUI for a hub application.

FIG. 13 illustrates an exemplary methodology 1300 relating to a hub application acting as a platform by way of which multiple supplement applications can be accessed. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

The exemplary methodology 1300 is performed by a client computing device that executes a client EHR and a hub application. As noted above, a GUI for the client EHR and a GUI for the hub application can be display concurrently on a display of the client computing device. The methodology 1300 starts at 1302, and at 1304, the GUI for the hub application is displayed on the display of the client computing device concurrently with the GUI for the client EHR. The GUI for the hub application includes a ribbon, wherein the ribbon includes a plurality of selectable buttons. As described above, the plurality of selectable buttons are representative of a plurality of supplement applications that interface with the hub application, wherein each of the supplement applications is configured to generate events based upon a current context of the client EHR. Thus, for instance, a supplement application can be a patient-centric supplement application, which can generate events that are specific to the patient (where the client EHR has data about the patient loaded therein). In another example, a supplement application can be a population-centric supplement application, which can generate events that are specific to a population (rather than a specific patient). In such an example, the client EHR can have data about a patient that belongs to a certain patient population loaded therein, the client EHR can have no patient-specific data loaded therein (e.g., the client EHR has data about the healthcare worker 104 loaded therein, but not about an individual patient).

At 1306, a selection of a button in the plurality of buttons is received, wherein the button represents a supplement application that interfaces with the hub application. At 1308, responsive to receiving the selection of the button, data generated by the supplement application is displayed on the display of the client computing device (e.g., concurrently with the hub application GUI or in the hub application GUI, and also concurrently with the client EHR GUI). For instance, when the supplement application is being executed in the background by the client computing device, the supplement application can be brought to the foregoing, and GUI elements produced by the supplement application can be rendered on the display. In another example, when the supplement application is not being executed by the client computing device at the time that the button is selected, the client computing device can launch the supplement application. The methodology 1300 completes at 1310.

Figure 14:
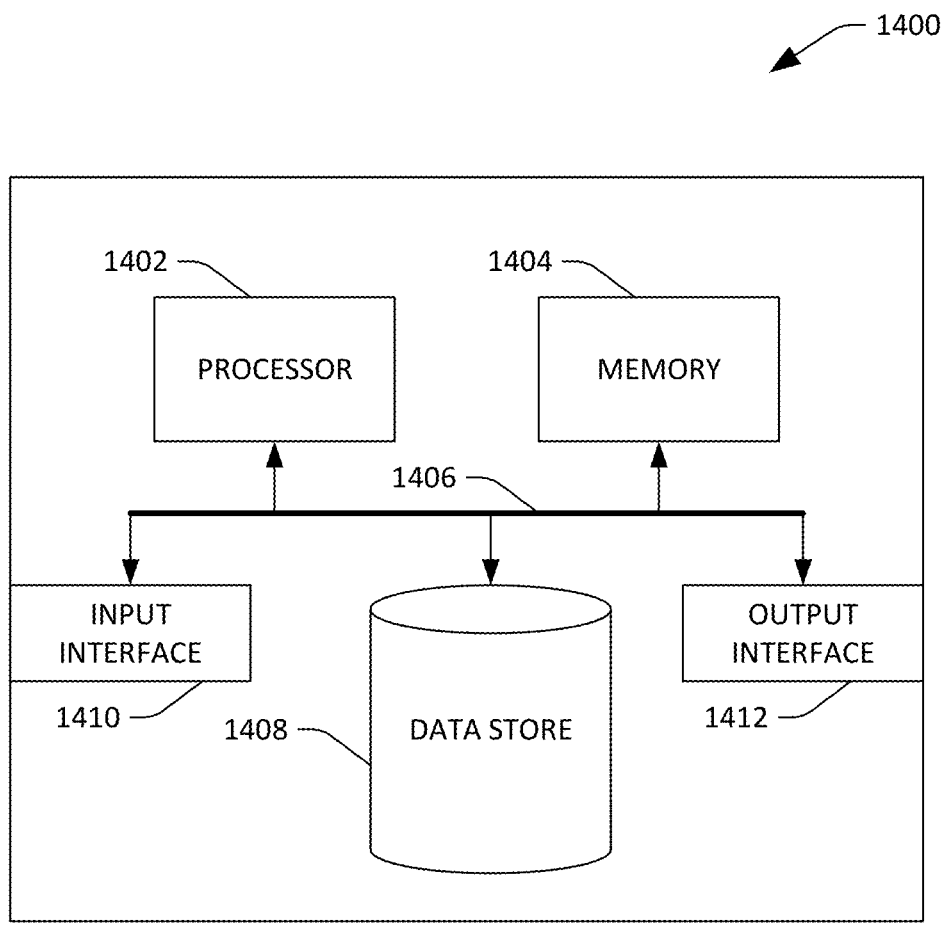
FIG. 14 is an exemplary computing system.

Referring now to FIG. 14, a high-level illustration of an exemplary computing device 1400 that can be used in accordance with the systems and methodologies disclosed herein is illustrated. For instance, the computing device 1400 may be used in a system that executes an EHR. By way of another example, the computing device 1400 can be used in a system that executes a supplement application and/or hub application. The computing device 1400 includes at least one processor 1402 that executes instructions that are stored in memory 1404. The instructions may be, for instance, instructions for implementing functionality described as being carried out by one or more components discussed above or instructions for implementing one or more of the methods described above. The processor 1402 may access the memory 1404 by way of a system bus 1406. In addition to storing executable instructions, the memory 1404 may also store patient-centric data, population data, etc.

The computing device 1400 additionally includes a data store 1408 that is accessible by the processor 1402 by way of the system bus 1406. The data store 1408 may include executable instructions, patient-centric data, population data, etc. The computing device 1400 also includes an input interface 1410 that allows external devices to communicate with the computing device 1400. For instance, the input interface 1410 may be used to receive instructions from an external computer device, from a user, etc. The computing device 1400 also includes an output interface 1412 that interfaces the computing device 1400 with one or more external devices. For example, the computing device 1400 may display text, images, etc. by way of the output interface 1412.

It is contemplated that the external devices that communicate with the computing device 1400 via the input interface 1410 and the output interface 1412 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1400 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1400 may be a distributed system. Thus, for instance, several devices may be in communication by way of a network connection and may collectively perform tasks described as being performed by the computing device 1400.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A client computing device operated by a healthcare worker, comprising:
   a processor;
   a display; and
   memory storing a hub application that, when executed by the processor, causes the processor to perform acts comprising:
      causing a graphical user interface (GUI) for the hub application to be displayed on a display of the computing device, wherein the GUI for the hub application comprises a ribbon that includes a plurality of selectable buttons, wherein each selectable button in the plurality of selectable buttons is representative of a different supplement application that is in network communication with the hub application, each supplement application executes on a respective computing device, wherein each supplement application outputs respective supplement data and maintains the respective supplement data in respective computer-readable storage, wherein the respective supplement data is supplementary to EHR data provided by a client electronic health records application (EHR) that is also being executed by the processor, and further wherein each supplement application is configured to report updates to the hub application based upon a current context of the client;
      receiving, from a supplement application in the plurality of supplement applications, supplement data output by the supplement application;
      receiving a selection of a selectable button in the plurality of selectable buttons, the selectable button is representative of the supplement application; and
      responsive to receiving the selection of the selectable button, causing the supplement data to be displayed on the display.

2. The computing device of claim 1, wherein the selectable button has a badge rendered thereon, and further wherein the badge indicates that the supplement application has reported an update that has yet to be reviewed by the healthcare worker.

3. The computing device of claim 2, wherein the badge identifies a number of updates reported by the supplement application that have yet to be reviewed by the healthcare worker.

4. The computing device of claim 1, wherein the ribbon further comprises an identifier for a patient, wherein the current context of the client EHR comprises EHR data for the patient that is displayed in a GUI for the client EHR that is also presented on the display.

5. The computing device of claim 1, wherein the ribbon comprises a first selectable button and a second selectable button, the first selectable button is representative of a first type of supplement application, the second selectable button is representative of a second type of supplement application, and further wherein each button in the plurality of selectable buttons represents a supplement application of the first type of supplement application.

6. The computing device of claim 5, wherein the first selectable button is highlighted in the ribbon to indicate that the plurality of selectable buttons displayed in the ribbon represent supplement applications of the first type of supplement application.

7. The computing device of claim 6, wherein the first type of supplement application is patient-centric, and wherein the second type of supplement application is population-centric, wherein patient-centric supplement applications are configured to report updates about a patient whose health information is loaded in the client EHR, and further wherein population-centric applications are configured to report updates about populations of patients.

8. The computing device of claim 7, the acts further comprising:
   receiving an indication that a population-centric supplement application has reported an update; and
   responsive to receiving the indication, rendering a badge on the second selectable button, wherein the badge indicates that at least one population-centric supplement application has reported the update.

9. The computing device of claim 5, the acts further comprising:
   receiving a selection of the second selectable button; and
   responsive to receiving the selection of the second selectable button, removing a first plurality of selectable buttons from the ribbon; and
   responsive to receiving the selection of the second selectable button, displaying a second plurality of selectable buttons in the ribbon, the second plurality of selectable buttons representing supplement applications of the second type.

10. The computing device of claim 1, wherein the current context of the client EHR comprises at least one of:
    an identity of a patient whose medical information is presented on the display by way of the client EHR; or
    an identity of the healthcare worker that is logged into the client EHR.

11. A method performed by a processor of a client computing device while the processor executes a hub application, the client computing device is operated by a healthcare worker, the method comprising:
    displaying a graphical user interface (GUI) for a hub application on a display, wherein the GUI for the hub application comprises a ribbon, and further wherein the ribbon comprises a plurality of selectable buttons, wherein each selectable button in the plurality of selectable buttons is representative of a different supplement application that is in network communication with the hub application, each supplement application executes on a respective computing device, wherein each supplement application produces respective supplement data and maintains the respective supplement data in respective computer-readable storage, wherein the respective supplement data is supplementary to EHR data provided by a client electronic health records application (EHR) that is also being executed by the processor, and further wherein the plurality of supplement applications are configured report updates to the hub application based upon a current context of the client;
    receiving, from a supplement application in the plurality of supplement applications, supplement data produced by the supplement application;
    receiving a selection of a selectable button in the plurality of selectable buttons, the selectable button is representative of the supplement application; and
    responsive to receiving the selection of the selectable button in the plurality of selectable buttons, presenting the supplement data on the display.

12. The method of claim 11, further comprising:
    responsive to receiving the selection of the selectable button in the plurality of selectable buttons, displaying a GUI for the supplement application that is represented by the button, wherein the supplement data produced by the supplement application is displayed in the GUI for the supplement application, and further wherein the GUI for the supplement application is displayed concurrently with the GUI for the hub application.

13. The method of claim 11, wherein the GUI for the hub application comprises the supplement data produced by the supplement application.

14. The method of claim 11, further comprising:
    prior to receiving the selection of the selectable button in the plurality of selectable buttons, receiving a report for an update from the supplement application; and
    responsive to receiving the report, rendering a badge on the button, the badge indicates that the supplement application has reported the update to the hub application.

15. The method of claim 14, wherein the badge indicates that the healthcare worker, who has authenticated with the client EHR, has yet to review the update reported by the supplement application.

16. The method of claim 11, further comprising displaying an identifier for a patient in the ribbon, wherein the identifier for the patient is received from the client EHR, and further wherein the client EHR is presenting EHR data about the patient on the display.

17. The method of claim 11, further comprising:
    displaying a first selectable button and a second selectable button in the ribbon, wherein the first selectable button is representative of a first type of supplement application, and the second selectable button is representative of a second type of supplement application; and
    highlighting the first selectable button to indicate that the plurality of supplement applications represented by the plurality of selectable buttons are supplement applications of the first type.

18. The method of claim 17, further comprising:
    receiving a selection of the second selectable button;
    responsive to receiving the selection of the second selectable button, removing the plurality of selectable buttons from the ribbon; and
    displaying a second plurality of selectable buttons in the ribbon, the second plurality of selectable buttons representative of a second plurality of supplement applications, wherein the second plurality of supplement applications are configured report updates to the hub application based upon the current context of the client EHR, and further wherein each supplement application in the second plurality of supplement applications are of the second type of supplement application.

19. The method of claim 17, wherein the first type of supplement application is patient-centric, and wherein the second type of supplement application is population-centric, wherein patient-centric supplement applications are configured to report updates about a patient whose health information is loaded in the client EHR, and further wherein population-centric applications are configured to report updates about populations of patients.

20. A computer-readable storage medium comprising instructions that, when executed by a processor of a computing device, cause the processor to perform acts comprising:

causing a graphical user interface (GUI) for a hub application to be displayed on a display of the computing device, wherein the GUI for the hub application comprises a ribbon that includes a plurality of selectable buttons, wherein each selectable button in the plurality of selectable buttons is representative of a different supplement application that is in network communication with the hub application, each supplement application executes on a respective computing device, wherein each supplement application outputs respective supplement data and maintains the respective supplement data in respective computer-readable storage, wherein the respective supplement data is supplementary to EHR data provided by a client electronic health records application (EHR) that is also being executed by the processor, and further wherein each supplement application is configured to report updates to the hub application based upon a current context of the client;

receiving, from a supplement application in the plurality of supplement applications, supplement data output by the supplement application;

receiving a selection of a selectable button in the plurality of selectable buttons, the selectable button is representative of the supplement application; and responsive to receiving the selection of the selectable button, causing the supplement data to be displayed on the display.

* * * * *